(12) United States Patent
Hacker et al.

(10) Patent No.: US 9,364,144 B2
(45) Date of Patent: Jun. 14, 2016

(54) METHOD AND DEVICE FOR RECORDING AND DISPLAYING AN OCT WHOLE-EYE SCAN

(75) Inventors: Martin Hacker, Jena (DE); Ferid Bajramovic, Jena (DE); Rico Fuchs, Jena (DE); Martin Kühner, Bad Klosterlausnitz (DE)

(73) Assignee: Carl Zeiss Meditec AG, Jena (DE)

( * ) Notice: Subject to any disclaimer, the term of this patent is extended or adjusted under 35 U.S.C. 154(b) by 568 days.

(21) Appl. No.: 13/825,786

(22) PCT Filed: Aug. 18, 2011

(86) PCT No.: PCT/EP2011/004154
§ 371 (c)(1),
(2), (4) Date: Mar. 22, 2013

(87) PCT Pub. No.: WO2012/038011
PCT Pub. Date: Mar. 29, 2012

(65) Prior Publication Data
US 2013/0242259 A1    Sep. 19, 2013

(30) Foreign Application Priority Data
Sep. 24, 2010   (DE) .......................... 10 2010 046 500

(51) Int. Cl.
*A61B 3/14* (2006.01)
*A61B 3/00* (2006.01)
(Continued)

(52) U.S. Cl.
CPC ............... *A61B 3/102* (2013.01); *A61B 8/5238* (2013.01); *A61B 8/10* (2013.01)

(58) Field of Classification Search
CPC ........ A61B 3/00; A61B 3/103; A61B 3/1225; A61B 3/113; A61B 3/1015
USPC .................. 351/206, 205, 221, 210, 200, 246
See application file for complete search history.

(56) References Cited

U.S. PATENT DOCUMENTS 4,881,808 A * 11/1989 Bille .................... A61B 3/1225
                                                    351/221
7,365,856 B2    4/2008 Everett et al.
(Continued)

FOREIGN PATENT DOCUMENTS

| DE | 10 2008 051272 A1 | 4/2010 |
|----|---|---|
| DE | 10 2008 063 255 A1 | 7/2010 |
| WO | WO 2010/009447 A2 | 1/2010 |

OTHER PUBLICATIONS

Lexer et al.; "Wavelength-tuning interferometry of intraocular distances"; Applied Optics vol. 36, No. 25, Sep. 1, 1997, pp. 6548-6553.
(Continued)

*Primary Examiner* — Dawayne A Pinkney
(74) *Attorney, Agent, or Firm* — Patterson Thuente Pedersen, P.A.

(57) ABSTRACT

The eye is illuminated by a variable laser light source with a measurement range corresponding to the eye length, wherein the focus of the laser beam in the eye can be shifted laterally and/or axially by an adjustment mechanism, and the light fractions back-scattered from the sample are captured via an interferometer by a data acquisition unit and forwarded to a data processing unit. In the data processing unit, an OCT whole-eye scan is combined with at least one or several further overlapping tomographic part-eye or whole-eye scans. Reference information is used to register the first whole-eye scan with the further part-eye or whole-eye scans, and the combined whole-eye scan is evaluated and/or displayed on a user surface.

37 Claims, 4 Drawing Sheets

(51) Int. Cl.
*A61B 3/10* (2006.01)
*A61B 8/08* (2006.01)
*A61B 8/10* (2006.01)

(56) References Cited

U.S. PATENT DOCUMENTS

| | | | |
|---|---|---|---|
| 2006/0187462 A1 | 8/2006 | Srinivasan et al. | |
| 2008/0100612 A1* | 5/2008 | Dastmalchi | G06F 19/321 345/418 |
| 2010/0110171 A1* | 5/2010 | Satake | A61B 3/102 348/78 |
| 2011/0255054 A1 | 10/2011 | Hacker et al. | |

OTHER PUBLICATIONS

Drexler and Fujimoto; "Optical Coherence Tomography Technology and Applications", Springer-Verlag, 2008, 2 pages.

Tang et al.; "Measuring total corneal power before and after laser in situ keratomileusis with high-speed optical coherence tomography"; J Cataract Refract Surg. Nov. 2006; 32(11): 1843-1850.

Huang D. et al.; "Anterior eye imaging with OCT"; in: "Optical Coherence Tomography"; Springer ISBN 978-3-540-77549-2, pp. 961-964.

Chong Ch. et al.; "Large coherence length swept source for axial length measurement of the eye"; Applied Optics vol. 48, No. 10, Apr. 1, 2009, pp. D144-D150.

Reinstein D. et al.; "Very high frequency ultrasound analysis of a new phakik posterior chamber intra ocular lens in situ", Brief Reports, vol. 125, No. 5, pp. 725-729.

Reinstein D, et al; "Correlation of anterior chamber angle and Ciliarly Sulcus diameters with white-to-ehite corneal diameter in high myopes using Artemis VHF digital ultrasound", Journal of Refractive Surgery, vol. XX, Month 200X, pp. 1-10.

* cited by examiner

METHOD AND DEVICE FOR RECORDING AND DISPLAYING AN OCT WHOLE-EYE SCAN

PRIORITY CLAIM

The present application is a National Phase entry of PCT Application No. PCT/EP2011/004154, filed Aug. 18, 2011, which claims priority to German Application No 10 2010 046 500.3, filed Sep. 24, 2010, the disclosures of which are hereby incorporated by reference herein in their entirety.

FIELD OF THE INVENTION

The invention is related to the field of ophthalmology and serves for displaying the anterior and posterior portions of the eye, in particular the whole eye, wherein the displays are preferably based on optical coherence tomography scans.

BACKGROUND OF THE INVENTION

Based on the demand or the desire of medical-diagnostic applications for displaying an anatomically correct overall image of the eye, different approaches are proposed in this connection in the known prior art.

In particular, the attempt was made to implement such displays by means of magnetic resonance imaging (MRI) and computed tomography (CT). The MRI has the disadvantage here that the resolution depends on the implementable magnetic field strength which, in turn, is mainly limited by the needed measuring volume. The resolution of the MRI, which lies in the mm-range, is in general not sufficient for high-precision diagnostic examinations on humans. CT, in turn, has the disadvantages of exposure to radiation and the need of costly equipment. Moreover, the contrasts for X-rays do not always correlate with the optically relevant variables in the visible wavelength range (such as refractive index transitions or scattering), which can be a problem in ophthalmology.

In contrast to that, better results can be achieved in the different eye regions by using optical measurement methods that are adapted to the respective eye regions. In the anterior region, these methods are, for example, the optical coherence tomography (anterior chamber OCT, AC-OCT) as well as slit lamp imaging and Scheimpflug imaging; in the posterior eye region, however, these methods are retinal optical coherence tomography and also confocal scanning and fundus imaging.

However, in the following, such approaches are addressed in which displaying the whole eye is based on at least one coherence tomography measurement which extends over the entire length of the eye.

The methods and measurement devices based on optical coherence tomography (OCT) are in the known prior art the most widely accepted solutions for tomographic imaging of eye structures.

In OCT methods, coherent light is used with the aid of an interferometer for distance measurement and imaging on reflective and scattering samples. During a scan into the depth on the human eye, due to changes of the refractive index occurring on optical boundary surfaces and due to volume scattering, the OCT methods deliver measurable signals. The optical coherence tomography is a very sensitive and fast method for interferometric imaging which has found broad acceptance in particular in the medical field and in basic research. OCT images (OCT scans) of eye structures are frequently used in ophthalmology for diagnosis and therapy monitoring, and also for planning of surgical interventions and for selecting implants.

The basic principle of the OCT method, as described, for example, in U.S. Pat. No. 5,321,501, is based on white-light interferometry and compares the transit time of a signal with the aid of an interferometer (primarily a Michelson interferometer). Here, the arm having a known optical path length (=reference arm) is used as a reference for the measuring arm in which the sample is located. The interference of the signals from both arms forms a pattern from which the scattering amplitudes can be determined in dependence on the optical delay between the arms, and thus a depth-dependent scattering profile can be determined which, analogous to ultrasonic technology, is designated as A-scan. In multi-dimensional raster methods, the beam is then guided transversally in one or two directions, as a result of which a two-dimensional B-scan or a three-dimensional volume tomogram can be recorded. Here, the amplitude values of the individual A-scans are represented in linear or logarithmized grey scale values or false color values. The technology of recording individual A-scans is also designated as optical coherence domain reflectometry (OCDR); in contrast to this, OCT implements two- or three-dimensional imaging through lateral scanning.

From the OCT methods used in ophthalmology, two different basic types have established themselves. For determining the measured values with the first type, the length of the reference arm is changed and the intensity of the interference is continuously measured without considering the spectrum. This method is designated as "time domain" method (U.S. Pat. No. 5,321,501 A). On the contrary, in the other method, the method designated as "frequency domain", the spectrum is considered when determining the measured values, and the interference of the individual spectral components is recorded.

Thus, on the one hand, this is referred to as signal in the time domain and, on the other, as signal in the frequency domain. The advantage of the "frequency domain" method is the simple and fast simultaneous measurement, wherein complete information about the depth can be determined without the need of movable parts. This increases stability and speed (U.S. Pat. No. 7,330,270 B2), as a result of which in particular three-dimensional OCT images have been made possible.

Furthermore, in the frequency domain OCT, a distinction is made whether the spectral information is obtained by means of a spectrometer ("spectral domain OCT", SD-OCT) or by means of spectral tuning of the light source ("swept source OCT", SS-OCT).

A great technological advantage of OCT is the decoupling of the depth resolution from the transversal resolution. Through this it is possible in particular in the case of limited numerical apertures to achieve a very good axial resolution, for example, so as to be able, despite aperture limitation by the pupil, to examine retina layers in the axial direction with high (<20 μm) and highest (<4 μm) resolutions. The contactless OCT measurement based on backscattering and reflection thus enables generating microscopic images in vivo. A further advantage is the efficient suppression of non-coherent portions of disturbing light. "Axial direction" means here the direction of the depth profile displayed in the A-scan. Due to local refractions, said direction can also vary in A-scan portions but is usually nearly parallel to the optical axis or to the visual axis from the cornea vertex to the fovea of an eye to be examined.

A first use of the display of the overall depth profile of the backscattering of the eye, which display is based on coherence reflectometry measurements (OCDR), is described by F. Lexer et al. in [1]. Here it is emphasized again that the exact knowledge of the intraocular distances is an important resource of modern ophthalmology, for example for matching intraocular lens implants. While the axial eye length and the depth of the anterior chamber are absolutely necessary for precise calculations of the refraction power of intraocular lenses for cataract surgeries, the accurate measurement of the corneal thickness is important for refractive surgery. For diagnosing various diseases and for monitoring the therapeutic effects, the determination of the thickness of the retinal layers can be helpful. The approach described in [1] is based on a SS-FD-OCDR system of medium quality and it allows measuring the distances of all optical surfaces in the eye over the entire length of the eye. While it was possible to achieve a good resolution with this approach when scanning the entire measuring range of model eyes, this was no longer possible for the simultaneous "in vivo" measurement of three intraocular distances. It has been found that the approach for measuring intraocular distances with an accuracy up to at best 30 µm achieves a sufficient resolution; however, for high-resolution OCDR or OCT applications, this approach is no longer suitable.

In the published applications US 2007/216909 A1, US 2007/291277 A1 and US 2008/100612 A1, SD-OCT systems are described which comprise a switchable focus and/or a switchable reference plane (zero-delay) of the OCT arrangement. Here, during a retinal scan, the focus should lie in the region of the retina, and during a corneal scan, the focus should lie in the region of the cornea. In this manner, an OCT scan with high lateral resolution of the anterior or posterior portion of the eye is possible. Furthermore, it is described that a retinal scan with the rotation point of the scan being in the iris/pupil plane is advantageous. With the solutions proposed here, two-dimensional scans with high resolution as well as three-dimensional scans (data cubes) can be recorded and evaluated.

The object to be achieved here was to make OCT scans possible in each case with high resolution and high signal strength of the anterior and also the posterior portions of the eye and with only one device. No proposal for a solution for the implementation of whole-eye scans or for the combination of retinal and corneal scans so as to form a single image of the eye was disclosed.

Another "frequency domain"-based OCT system is described by Walsh et al. in WO 2010/009447 A2. The spectral information is obtained either by means of a spectrometer (SD-OCT) or by means of a spectrally tunable light source (swept source, SS-OCT). Hereby, the eye can be displayed in a plurality of portions along the optical axis or also completely by means of A-, B-, or C-scans. The solution describes a method for a whole-eye scan and also for consecutive partial scans. Here too, the scan rotation point in the pupil needed for a retinal scan is emphasized. Furthermore, many possible opthalmological applications of whole-eye scan are described.

Furthermore, WO 2010/009447 A2 describes the apparently practicable combination of a plurality of OCT scans by means of fast whole-eye scout scans or "via stitched" scans via mathematical AND or OR operators.

However, WO 2010/009447 A2 does not describe the different types of displays in the scan data resulting from the scan modalities, and no solution for a necessary registration of the data to one another is described. However, an AND or OR conjunction can only be applied after a sufficient registration of the scan to one another has been performed. A registration is to be understood as an allocation of corresponding structures which are included in different scans, and also, based on said allocation, as a spatial alignment and matching of scans with each other, in particular for an easier visualization, analysis and motion correction (U.S. Pat. No. 7,365,856 B2).

The solution described in WO 2012/009447 A2 is therefore not practicable since such a combination on the basis of AND or OR operators is only possible after a suitable spatial alignment, dewarping and matching of the scans, which, however, is not disclosed.

In WO 2010/009447 A2, the desired information is contained not only one but in a plurality of display formats. The measurement conditions used for this can even result in different images of the individual regions which are difficult to compare with each other. For example, depending on the position, scans or partial scans can contain angularly and spatially resolved signals. Thus, a scan of the anterior chamber, which scan is telecentric outside of the eye, is inevitably subjected to spatial distortions after the refraction on the cornea, which distortions allow a combination with a scan carried out in a deeper eye plane only after consideration of this refraction.

With the OCT system proposed in WO 2010/009447 A2, merely a solution is proposed with which at best non-dewarped, spatially unmatched A-, B- or C-scans of anterior and posterior eye portions or also individual whole-eye scans of medium or poor signal quality and low, inhomogeneous lateral resolution can be displayed together in a manner unsuitable for diagnostic or biometric purposes.

In particular, no solution is given in order to combine scans of the anterior and posterior eye portions optimized with regard to signal strength and lateral resolution in such a manner that an anatomically correct or true to scale display of the whole eye is implemented, which display is robust with respect to eye movements and is optimized for diagnostic or biometric measures.

Spatial dewarpings of OCT scans on corneas are described, for example, by Drexler and Fujimoto in [2]. Further known are observations of ray paths in eyes having a known geometry as a means for selecting intraocular lenses by means of ray tracing or matrix formalism, as described by Tang et al. in [3].

The necessity to bring the scan rotation point into the pupil/iris plane for measurements behind the pupil is also discussed in more detail by D. Huang et al. in [4]. Thus, vignetting of large angular ranges caused by the pupil during scanning can be largely avoided. In contrast to this, anterior scans are not carried out with a pivot point in the pupil plane so that also the front and back sides of the lens can be spatially resolved. In this connection it was found that retinal OCT scanners are principally suitable for scanning the anterior eye segments, but that the low scanning speed and the typically used near infrared light are disadvantageous. For scanning the anterior transparent eye segments, on the one hand, wavelengths of about 1310 nm prove to be much more effective. On the other hand, in addition to concentric or telecentric scan geometries, sector-shaped scan geometries are also used here.

The OCDR system described in DE 10 2008 051272 A1 serves for the interferometric measurement of eye portion lengths over the entire eye length. A laterally scanning OCDR system is described in which also the focus is variable or switchable in order to implement optimal A-scan signals by means of combination. No solution for the anatomically correct display of combined part-eye or whole-eye OCR scans is proposed. The radiation backscattered from the boundary surfaces of the eye is interferometrically acquired and through time domain-, spectral domain- or Fourier domain-coherence reflectometry, a measurement signal is generated that indicates structures of the eye. With this OCDR system, a solution is made available with which preferably a plurality of high-precision sectional measurements on the eye shall be carried out simultaneously. With the proposed OCDR system, a solution is made available with which eye portion lengths can be measured with high precision over the entire length of the eye. Tomographic OCT recordings of the anterior and posterior eye portions by means of A-, B- or C-scans are not possible with this system.

An OCDR system based on long-coherence-length, tunable lasers (swept-sources) with a scan depth of more than 40 mm in tissue has been proposed in DE 10 2008 063 225 A1. With this system, particularly good signal conditions and low motion sensitivity at all boundary surfaces of the eye can readily be implemented even in the case of very long eyes, as is also shown by an example.

An OCT system based on a swept source with relatively large coherence length and with a depth range of nearly 35 mm is described by Ch. Chong et al. in [5]. With the proposed approach it is principally possible to implement tomographic pictures of the whole eye, on which pictures the contours of cornea, iris, lens and retina are visible to some degree.

However, in the case of an experimental implementation, details of the segments exhibit poor visibility because the implemented lateral resolutions and the signal strengths are rather low. Because of the significant signal drop due to the insufficient coherence length of the source of only 28 mm, only pig eyes with a geometrical length of ca. 20 mm could be measured. For human eyes with a geometrical length of up to 40 mm, this system is insufficient.

As described in the prior art, for OCT scans in the whole eye region it is necessary to position the measuring beam focus in the eye portion to be scanned. The size of the focus is important for the resolution as well as for the signal strength of the measurement signal. Thus, for anterior measurement, the focus should lie in the anterior eye region or even in front of the eye, and for posterior measurements, it should lie in the posterior eye region. In this context, on the one hand, different device-related measurement conditions such as focusing, reference plane (zero delay) and scanning can result in different images of the individual regions, inclusive distortions and different magnification factors. On the other hand, this can also be a result of patient-related different fixation, accommodation or movement.

Furthermore, eye structures can exhibit different double refraction which can result in differences in terms of the polarization characteristics of the light backscattered from the individual structures, and thus can result in signal conditions in the scans which are dependent on the polarization settings.

Furthermore, Reinstein et al. describe in [6] and [7] depth-resolved eye scans by means of which regions in the eye can be displayed which cannot be displayed by means of OCT. Known in the prior art are, for example, high-resolution ultrasound displays of anterior regions of the eye including the peripheral regions of the eye lens behind the iris, or the position of IOLs including the haptics behind the iris. A registered combination of ultrasound data or other tomographic data with OCT data is not described, but would be of interest for several medical-diagnostic applications (inter alia, biometry).

Besides the registrations of OCT scans among each other, there is also the possibility of spatial referencing and correction by means of reference information from other, non-depth-resolving measurement systems, for example, with height information from topographs, as described by Tang et al. in [3]. Besides sectional measurements, topographies or kerarometries are necessary parameters for matching refractive intraocular implants such as IOLs.

LITERATURE

[1] Lexer et al.; "Wavelength-tuning interferometry of intraocular distances"; APPLIED OPTICS Vol 36, no. 25, Sep. 1, 1997

[2] Drexler and Fujimoto; "Optical Coherence Tomography Technology and Applications", Springer-Verlag, 2008

[3] Tang et al.; "Measuring total corneal power before and after laser in situ keratomileusis with high-speed optical coherence tomography";
J Cataract Refract Surg. 2006 November; 32(11): 1843-1850

[4] Huang D. et al.; "Anterior eye imaging with OCT"; in: "Optical Coherence Tomography"; Springer ISBN 978-3-540-77549-2

[5] Chong Ch. et al.; "Large coherence length swept source for axial length measurement of the eye"; APPLIED OPTICS Vol. 48, no. 10, Apr. 1, 2009

[6] Reinstein D. et al.; "Very high frequency ultrasound analysis of a new phakik posterior chamber intra ocular lens in situ"

[7] Reinstein D, et al; "Correlation of anterior chamber angle and Ciliarly Sulcus diameters with white-to-ehite corneal diameter in high myopes using Artemis VHF digital ultrasound"

SUMMARY OF THE INVENTION

For the different possible medical applications described in the prior art, anatomically correct or diagnostically problem-related images of OCT data are important. Without correct optical dewarping of the OCT scans, some of the applications described in the prior art deliver results that are not usable. Meaningful comparisons of data of different eyes and/or different measurements of an eye are often only possible in the case of dewarped displays.

A disadvantageous effect of the solutions according to the prior art is that none of the solutions discloses or suggests a registration of data from different scan modalities when linking and/or combining an OCT whole-eye scan with a further or a plurality of part-eye or whole-eye scans so as to form a tomographic image of the whole eye. However, this would be extremely advantageous since the whole-eye scan exhibits high robustness with respect to eye movements whereas part-eye scans can deliver good signal conditions in those regions in which the whole-eye scan is not able to do this due to the scan geometries and optical conditions.

It is therefore an object of the present invention to develop a solution for displaying tomographic images of the whole eye, which solution solves the disadvantages of the solutions of the known prior art and in which, based on interferometric measurement methods, all regions of the whole eye include depth-resolved, high-precision measurement data. At the same time, the display of the tomographic images of the whole eye shall be carried out anatomically correct, i.e., with correct dimensions and distances of the individual eye segments, or in diagnostically problem-related manner, i.e., with axial and/or lateral stretching of eye part portions and nevertheless correct eye portion lengths.

With the method according to the invention for displaying tomographic images of the whole eye, based on the swept source optical coherence domain reflectometry (SS OCDR), in which the eye is illuminated by a tunable laser light source with a measurement range corresponding to the eye length, wherein the focus of the laser beam in the eye is laterally and/or axially displaceable by an adjustment mechanism, and the light fractions backscattered from the sample are captured via an interferometer by a data acquisition unit and are transferred to a data processing unit, this object is achieved in that in the data processing unit, an OCT whole-eye scan is combined with at least one or a plurality of further overlapping tomographic part-eye or whole-eye scans, reference information is used for registering the first whole-eye scan with the further part-eye or whole eye scans, and the combined whole-eye scan is evaluated and/or displayed on a user interface. In this context, the first OCDR or OCT whole eye scan and also one or a plurality of further part-eye or whole-eye scans are recorded as A-, B-, or C-scan.

The corresponding device for recording and displaying an OCT whole-eye scan, based on swept source optical coherence domain reflectometry (SS OCDR), consists of a tunable laser light source with a measurement range corresponding to the length of the eye, an interferometer with scan unit, an adjustment mechanism for laterally and/or axially displacing or switching the focus in the eye, a data acquisition unit for capturing the light fractions backscattered from the sample, and a data processing unit. Here, the data processing unit is designed for combining an OCT whole-eye scan with at least one or a plurality of further overlapping tomographic part-eye or whole-eye scans by using reference information for registering the first whole-eye scan with the further part-eye or whole-eye scans, for evaluating it and displaying it via an existing graphic user interface.

The present technical solution relates to the field of ophthalmology and serves for displaying the anterior and posterior portions of the eye, in particular the whole eye. Since the displays are preferably based on optical coherence tomography scans, the main use lies in ophthalmological diagnostics and therapy and the preparation and follow-up examinations of surgical interventions.

BRIEF DESCRIPTION OF THE DRAWINGS

The invention is described in more detail hereinafter by means of exemplary embodiments. In the figures.

DETAILED DESCRIPTION

Figure 1:
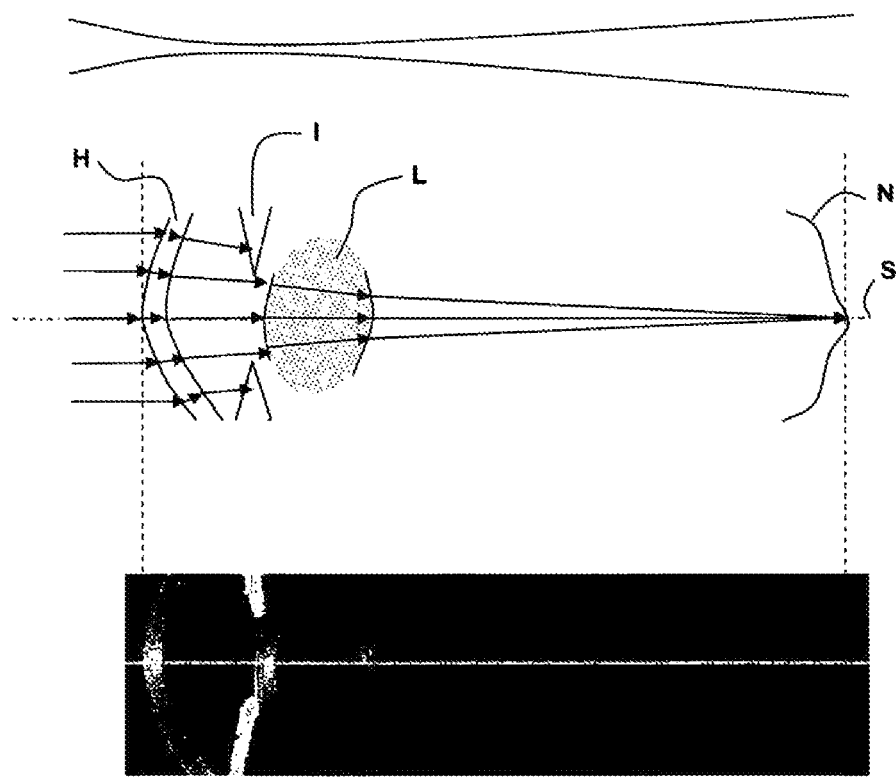
FIG. 1 depicts a possible scan process of an anterior scan.

With the method according to the invention for recording and displaying an OCT whole-eye scan based on swept source optical coherence reflectometry (SS OCDR), the eye is illuminated by a tunable laser light source with a measurement range corresponding to the eye length, wherein the focus of the laser beam in the eye is laterally and/or axially displaceable by an adjustment mechanism, and the light fractions backscattered from the sample are captured via an interferometer by a data acquisition unit and are transferred to a data processing unit.

In this context, an OCT whole-eye scan is combined by the data processing unit with at least one or a plurality of further overlapping tomographic part-eye or whole-eye scans, reference information is used for registering the first whole-eye scan with the further part-eye or whole eye scans, and the combined whole-eye scan is evaluated and/or displayed on a user interface.

For example, the first OCT whole-eye scan consisting of B- and C-scans is generated from A-scans which were detected in each case with a sensitivity above 90 dB during a measurement time of less than 30 ms, preferred less than 10 ms, and particularly preferred less than 1 ms, for which purpose preferably SS-OCDR technology is used. As is well known to the person skilled in the art, sensitivities can be determined, for example, by determining the signal-to-noise ratio of the maximum measurement signal of a reflector in consideration of the attenuation used.

The further part-eye or whole-eye scans are, for example originated from tomographical measurements such as, for example:
high-resolution ultrasound measurements (UBM),
SS-OCT (swept source optical coherence tomography) at wavelengths of about 1.3 µm,
SD-RT-OCT (spectral domain with spectrometer) at wavelengths of 700 nm to 900 nm, or
the identical or the same SS-OCT as the first whole-eye scan.

By a scan unit, an OCT whole-eye scan in the form of A-, B- or C-scans of the whole eye is implemented and is transferred together with one or a plurality of further part-eye or whole eye scans to the data processing unit. The data processing unit registers, in consideration of reference information, the individual scans transmitted from the data acquisition unit and combines two or more scans so as to form a tomographic image of the whole eye. The scans can be evaluated and/or displayed via a graphic user interface. Here, different scan patterns with different reference arm or sample arm lengths are used for anterior and posterior scans.

The reference information can be originated from the scan data itself, or additional data can be entered by the user, or can be uploaded from storage media, or can be transmitted from processors. The reference information can be obtained from the position detection of corresponding structures in the scans, and/or from the relation of the optical axis of the measurement system to the eye obtained from the data of the storage unit, calculating unit or input unit. Reference information is information about the position and the curvature of the anterior cornea surface and its distance to the RPE layer in the fovea centralis, which information is needed for optical dewarping and anatomically correct display. In this context, the specular boundary surface reflexes, in particular of front and back surfaces of cornea and eye lens or of the retina, which are easily detectable in the first and further OCT scans, are suitable as reference information. However, said reference information about the optical axis of the measurement system can also comprise offsets from calibration data, alignment data of measurement devices or user input data.

For displaying the whole eye, an OCDR or OCT whole-eye scan, consisting of one or a plurality of A-scans which have to comprise the whole eye, is combined with one or a plurality of anterior and posterior B- or C-scans which consist of a plurality of laterally displaced A-scans, wherein each A-scan can comprise a part of the eye or also the entire eye length.

Preferably, the further part-eye or whole-eye scans overlap at least over a tissue depth of more than 25 mm, but in one embodiment more than 32 mm or in a further embodiment more than 40 mm in the axial direction with the first OCT or OCDR whole-eye scan.

Such an overlap means that in all scans to be registered anterior structures (e.g. of the cornea or lens) as well as posterior structures (e.g. of the retina) are detectable, even if these structures possibly do not exhibit in all scans a quality suitable for the display. However, if in all scans to be combined the reference structures are contained, for example, in the form of boundary surface signals from the anterior and posterior eye regions, a particularly secure and highly accurate registration between the scans themselves can take place. Due to the redundancy and averaging effect, the simultaneous availability of anterior and posterior reference structures enables increased accuracy and increased reliability, for example, also through consistency considerations with a limited acceptable range.

The required minimal overlap length of 25 mm allows such a registration of a majority of the patients, in particular such patients with emmetropic and hyperopic eyes, since the average eye length is approx. 24 mm. With an overlap of at least 32 mm, nearly all patients can be considered, thus also those with pronounced axial myopia. Furthermore, with overlap lengths of over 40 mm it is also possible to cover extreme cases which, however, are rather rare (for example, buphthalmos).

Another advantage of the combination of OCT scans with overlaps>25 mm is that in the case of a common display, a delimitation of anterior and posterior scans arranged in a row in both scans can be defined in a common space in which there are no relevant structures so that in particular with regard to matching an IOL, no loss of information occurs. Such losses of information can occur if there would be signals of the cornea, retina or of natural or artificial eye lenses at the delimitation line of the scans to be combined.

The region for an advantageous delimitation can be defined, among other things, through the detection of the noise level. Suitable regions are regions between the boundary surfaces in which little/no volume scattering is detected, as, for example, in the vitreous. The delimitation between the scans does not have to correspond to a straight line but can be free in terms of the shape. If signals in the vitreous hinder such a definition of the delimitation between the scans, for example, as a result of hemorrhaging, the delimitation can also be carried out with regard to the cornea and the known or expected eye length in the vitreous region.

In the case of the swept source optical coherence domain reflectometry (SS OCDR) used here, during the A-scan, the data along the path of the beam of the tunable laser light source are plotted in a depth-resolved scatter profile. Here, the anatomically correct position of the intensity values of the A-scan depends on the actual path of the beam in the eye and thus on one or a plurality of the following parameters which, however, represent only an exemplary (but incomplete) list:
distance from the eye,
position of the scan rotation point in the eye,
eye lengths and eye part distances,
piercing angle to the refractive layers in the eye,
refractive index and course of the refractive index of the tissue in the eye,
axial and lateral resolution of the OCT scans,
numeric sampling of the scans in B- and C-scans,
position of the visual axis of the eye during the scan,
ametropia of the eye,
pachymetry and thickness of the cornea and its topography.

As has already been found in the prior art, it is advantageous for OCT scans in the entire eye region to position the measuring beam focus in the eye portion that is to be scanned in each case. With the method according to the invention, it is possible to use different scan patterns with different reference arm lengths of the interferometer for anterior and posterior scans.

The position of the reference plane of the OCT system according to the invention preferably remains the same for anterior and posterior OCT scans; however, it can also be configured to be discretely switchable or continuously variable, for example for minimizing signal drops. Preferably, even in the case of variations of the position of the reference plane, the reference arm length of the interferometer is kept constant while the sample arm length is changed, as a result of which the signal stability is increased.

In contrast to this, the polarization settings of the two or more scans can differ from each other in order to optimize the signal conditions in the individual scans.

The fixation of the eye is preferably centered and the B-scans preferably intersect the visual axis of the eye in the region of the cornea apex. Refixings for increasing the likelihood of generating specular boundary surface reflexes with high signal strength are possible but are not absolutely necessary.

For measuring the whole eye, apart from A-scans, it is also possible to use B- or C-scans with different scan patterns in the lateral direction such as, for example, line and curvature scans, meridian or star scans, circle scans, spiral scans, block scans etc. As mentioned, apart from the lateral scan configuration, focusing-dependent beam divergences and depth-dependent location and angle variations are also essential characteristics of a scan process.

Figure 2:
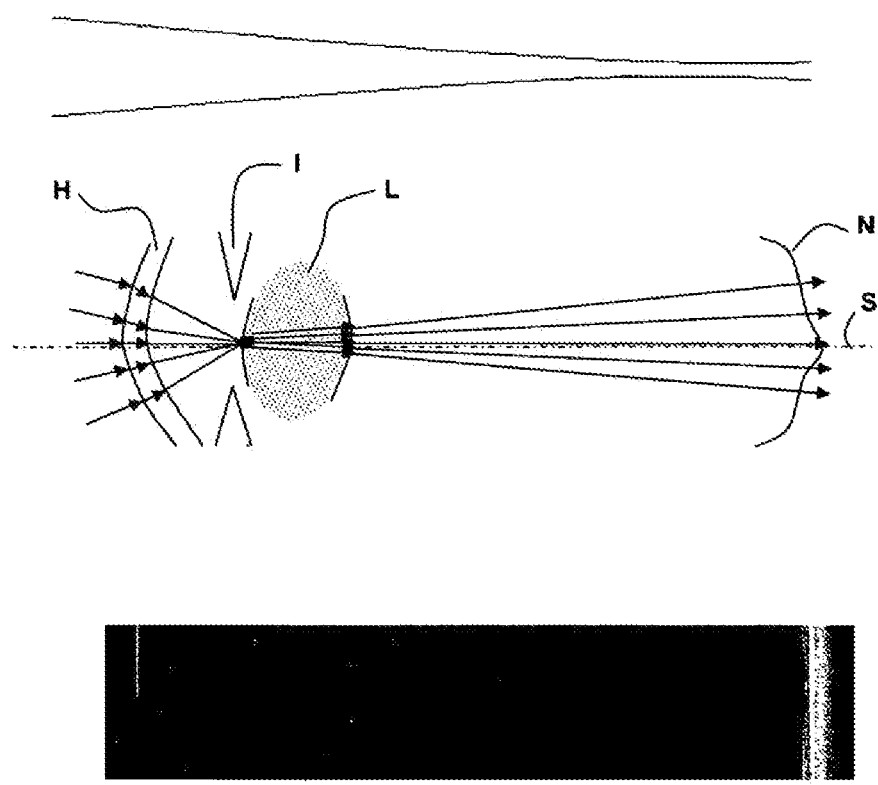
FIG. 2 depicts a possible scan process of a posterior scan.

To this, FIG. 1 and FIG. 2 show two exemplary line scan processes in the anterior and posterior eye region with the associated B-scans which range from whole scans to high-resolution scans layered along the optical axis. These two scan patterns already show a greatly differing beam path during scanning and also in terms of the beam shape.

FIG. 1 shows a possible scan process for an anterior scan, the focusing of which lies in the anterior eye portion so as to be able to generate there a good spatial resolution. The scanning beam runs through the cornea H and the lens L up and onto the retina N, wherein S characterizes the visual axis, and I characterizes the iris. While in the upper part the beam waist is illustrated, and in the middle part a possible beam path is schematically illustrated in dependence of the distances of the eye layers, the lower part shows the associated B-scan.

In the B-scan, the good spatial resolution of the anterior eye portions is shown while the retina is visible as a line, but actually is primarily an angularly resolved and not a spatially resolved image of the fovea. For the anterior scan, usually, a parallel or preferably a telecentric scan pattern is used.

In contrast to this, FIG. 2 shows in addition to the beam waist a possible scan process of a posterior scan. The scanning beam runs through the cornea H and the lens L up to and onto the cornea N, wherein S characterizes the visual axis, and I characterizes the iris. Here too, the upper part illustrates the possible beam path of a posterior scan which, as it is known from the prior art, has a scan rotation point in the pupil plane. The lower picture shows again the associated B-scan. Since here due to the widened beam and the scan pattern primarily no spatial resolution but primarily an angular resolution can be achieved in the anterior eye portions, the cornea and lens reflexes are only visible as line-like boundary surface reflexes. However, the retina located in the focus of the scanning beam can be displayed in a spatially resolved manner.

Thus, the focus of the scan preferably lies axially in the region that is in each case better suited for lateral resolution, i.e., in the case of the anterior scan in the vicinity of the anterior lens surface and in the case of the posterior scan in the vicinity of the retina.

The lateral width of the boundary surface structures in the scans depends in this method on the entered or measured or predefined eye parameters. According to the invention, the eye parameters comprise one or a plurality of the following parameters:
- eye lengths or eye part distances,
- refractive indices and course of the refractive indices,
- axial and lateral resolution of the OCT scans,
- position of the visual axis to the optical axis of the measurement system,
- topography or
- pachymetry of the eye.

In this context it is known to the person skilled in the art that refractive indices are to be understood as group velocity indices which are suitable for determining geometrical lengths from optical delays in consideration of dispersion.

The axial and lateral resolutions of the OCT system are considered here as eye parameters because the effective resolution in different regions of the eye depends on the geometric and optical conditions in the eye. For example, the lateral optical resolution in the region of the retina in a myopic eye is lower than in an emmetropic eye because here, defocussing takes place in the myopic eye. This can be taken into account when combining scans in order to implement the best possible displays of the eye with regard to resolution and signal strength.

In a first example configuration, the eye part distances to be considered by the data processing unit during the registration can be measured, preset or can be entered by the user as a defined axis length.

The eye part distances which are used here for the entire or partial correction of the overall displays can comprise, for example:
- the total length of the eye (distance from cornea to retina),
- the depth of the anterior chamber (distance from cornea to the front side of the lens),
- the cornea thickness or pachymetry,
- the lens thickness, or
- the distance from the lens to the retina.

In a particular configuration, the eye section distances can also be originated from the detection of the boundary surfaces of the OCT scan itself.

In an example case, registering is carried out over at least one SS OCT whole-eye scan with one or a plurality of further part-eye or whole-eye scans by means of registering via reference information. Registering the individual scans transmitted from the data acquisition unit is carried out in axial and/or lateral and/or rotatory manner and in consideration of information.

The visual axis, which is determined in the measurement device through the position of the fixation target, is indicative for the position of the optical axis of the measurement device in relation to the eye. If the positional relation between optical axis of the measurement device and the fixation axis of the eye is known, one or a plurality of OCT scans can be registered. At least 2 reference points and the optical axis of the two OCT scans must be known.

In the example case, the 2 points include specular boundary surface reflexes which can be detected in the scans to be registered. The specular reflexes can be detected in a whole-eye scan with anterior and also posterior modalities. They can be registered with known reference points of cornea vertex, fovea and further reference points.

Furthermore, it is also preferred that in addition an offset can be used for registering. This lateral or axial offset can consist of calibration, switching the scan modality, and entered x-, y- and z-coordinates. Data input, for example of stored calibration data or measured alignment data of measurement devices, can take place via user input or through a hardware or software data interface.

Figure 3:
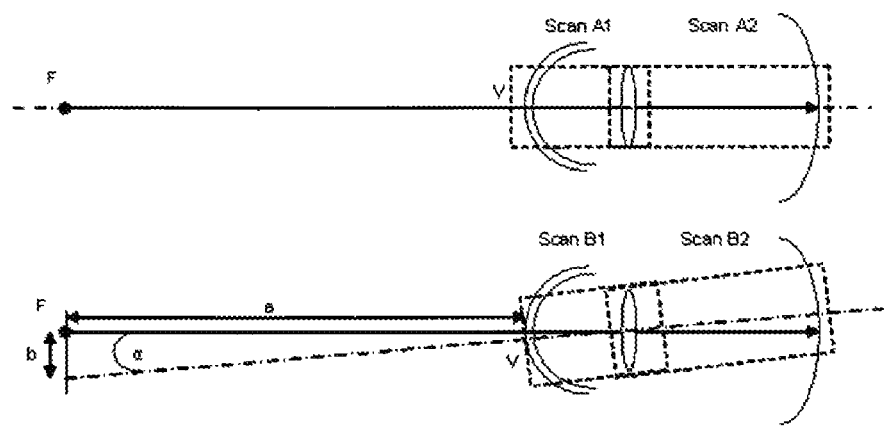
FIG. 3 depicts two possibilities for registering 2 OCT scans.

In this connection, FIG. 3 shows two possibilities for registering 2 OCT scans. Here, the registration is dependent on the position of the fixation axis (visual axis) in relation to the eye. Based on the fixation target F and the fixation axis, a conclusion is drawn on the position of the optical axis of the measurement device in relation to the cornea vertex V of the eye.

In the upper variant illustrated in FIG. 3, the fixation axis of the eye coincides with the optical axis of the measurement device so that the fixation target F likewise lies on the optical axis of the measurement device.

Figure 4:
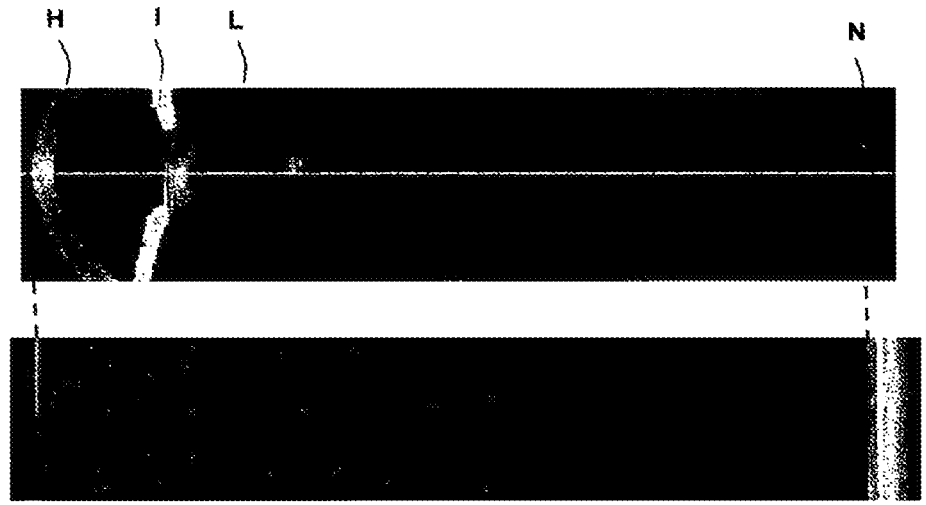
FIG. 4 depicts two registered OCT scans to be combined.

In contrast to this, in the lower variant shown in FIG. 4, the optical axis does not lie on the fixation axis. For registering the individual scans (A–A2 and B1–B2=), the distance b of the fixation target F from the optical axis and also the distance a of the eye from the measurement device or from the fixation target F have to be determined.

With the knowledge about the position of the fixation axis in relation to the eye, all scans can be registered to each other:
- A1 and A2,
- A1 and B2,
- B1 and A2 or
- B1 and B2.

Registration of the individual scans is carried out, for example, axially, i.e., along the optical axis or fixation axis, wherein anterior and posterior reflexes are used for this purpose. While the anterior reflex comprises the corneal vertex reflex, the posterior reflex comprises the fovea reflex of the retina.

It is particularly advantageous if most of the B-scans, ideally each of the B-scans (the A-scans of which each run through the entire depth of the eye) runs through the vertex of the cornea or through the piercing point of the visual axis through the cornea. In this case it is ensured that each B-scan includes anterior and posterior reflexes of defined eye part length portions which are used for axial registration.

It can be useful to select those B-scans from the measured B-scan which comply with the above advantageous condition. This can be controlled by monitoring the fixation state or the topography/keratometry as part of the lateral and rotatory registration during the recording of the B-scan.

Also, for the lateral registration with central patient fixation, the evaluation of simple reflexes such as fovea reflex and cornea vertex reflex is sufficient. Advantageously, the reflexes are detected from the OCT scans themselves, e.g., through threshold observation of scattering intensities and/or edge recognition and/or layer segmentations.

In contrast to lateral registration, rotatory registration of scans requires extraction of features from lateral structures or surfaces. For this, primarily iris structures, scleral blood vessel structures, boundary surface shapes or also topographies are evaluated.

While the iris or blood vessel structures are obtained from images recorded parallel or intermittent to the OCT scans, the boundary surface shapes can be obtained from the OCT scans themselves.

If topographies of the eye are to be evaluated for the rotatory registration, they can be recorded by means of Placido disk systems or can be retrieved for the respective eye.

In particular for possible medical applications it is important that displays of body parts, in particular of parts of the eye, are represented in an anatomically correct manner so as to be comparable, for example, with histological sections. Of course, this applies also to tomographic images in the form of OCT scans.

As has already been found in the prior art, the comparison of data of different eyes or of a plurality of measurements of the same eye is often only useful in the case of dewarped displays. Since this applies in particular also to OCT scans and due to the inevitably incorrect results, combining two of the described OCT scans makes little sense without a prior correct optical dewarping, or could even result in misinterpretation of diagnoses because structures located posterior to refractive surfaces can appear as being unusually deformed. The line display of the angularly resolved fovea in FIG. 1, which can easily be misinterpreted, has already been mentioned as an example.

As a requirement for correct dewarping it is assumed for all OCT scans that the beam path of the measurement system in front of the cornea is known through calibration of the OCT scanner or through measurements on a reference object. Subsequently, optical dewarping as a requirement for correct registration of the individual scans can be carried out in the axial and lateral directions so that the beam paths of the scans are known with regard to a common coordinate system.

Preferably, the individual OCT scans are spatially dewarped by means of optical beam tracing. Here, the known paths of the measuring beams are viewed during the scan up to the first refractive surface (cornea). Taking into account the known, measured or estimated shape of the refractive surface (at least 2-dimensional, preferably 3-dimensional) and the assumed or measured refraction index transition, now, the angle and divergence changes in the individual measuring beam paths are calculated by using, for example, the Snell's law of refraction or the Fermat's principle, so that depending on the depth, the signals of the A-scan can be allocated correct lateral spatial information. These considerations can now be continued on further refractive structures up to the retina (natural crystal lens, IOL). By considering measured or estimated refractive indices between the boundary surfaces, it is possible, in turn, to correct the eye part distances between the boundary surfaces in such a manner that they are geometrically correct. If, in some cases, the boundary surfaces cannot be detected, for example, because only parts are scanned or because highly absorbent tissue parts or scattering tissue parts cause shading, then, detected boundary surface parts are preferably interpolated and are extrapolated at least up to the A-scan which runs through the pupil margin. Otherwise, no correct dewarping of the scanned parts of the posterior eye portion is possible and there is the risk of generating artifacts. Suited for this are mathematical functions such as, for example, polynomials, splines or Fourier series.

With the lateral information allocated in this manner to the A-scan and with axial corrections, it is now possible by entering intensity signals into a common coordinate system to register correctly dewarped part-eye or whole eye B-scans to each other. It is possible here to average the intensity values of the individual scans in a weighted manner or to select them according to criteria such as the local signal-to-noise ratio.

It is also to be considered that in the case of the consideration of directional changes due to refraction and also in the case of axial corrections of distances, the dispersion of the refractive index of the tissue in dependence on the wavelength of the measuring beam should be taken into account. This wavelength of the measuring beam can also vary between the individual part-eye or whole-eye scans. For example, a whole-eye scan is preferably implemented with measurement radiation in the range between 1030 and 1090 nm, whereas the anterior eye portion is preferably measured in the range of from 1250 . . . 1400 nm or 750 . . . 900 nm, and the posterior eye portion is preferably measured in the range of from 750 . . . 900 nm.

For the case that the keratometry or topography of the cornea is known, it is possible through ray tracing to precisely determine the corrected ray path. In the best case, the accommodation state of the lens is also determined in the one or a plurality of scans, or is determined through simulation. Here, ray tracing is used for all A-scans. By considering the optical properties of boundary surfaces in the eye, the ray tracing performed along the ray propagation direction for each A-scan is utilized for dewarping the B- or C-scan.

For dewarping, one or a plurality of the above-mentioned parameters can be used. These parameters can be determined from the OCT scan itself or can be originated from other measurements, or can be defined and set by the user.

In this connection, FIG. 4 shows two registered OCT scans to be combined. While the upper image shows the anterior whole-eye scan in the form of a B-scan, the lower image illustrates a posterior whole-eye scan, likewise as a B-scan. Here, H designates the cornea, L the lens, N the retina, S the visual axis and I designates the iris of the eye.

As is already shown in the FIGS. 1 and 2, the focusing lies always in the eye portion of which a good resolution is to be generated. The B-scan displayed in the upper image shows the anterior whole-eye scan in which the anterior eye portions exhibit a good spatial resolution. In contrast, the lower image shows the B-scan of the posterior whole-eye scan in which the retina is displayed in a good spatial resolution.

After the individual scan transmitted by the data processing unit have been registered in consideration of eye section distances, two or a plurality of scans can be combined to form a tomographic image of the whole eye. According to FIG. 4, this can be carried out in that the partial images with good spatial resolution are combined to form a tomographic image of the whole eye, wherein a plurality of different display possibilities arise.

Thus, the ray path of both scans is known in a common coordinate system from which a dewarped whole-eye scan can be calculated, for example, by replacing the region of the retina in the dewarped anterior scan by the corresponding region in the dewarped posterior scan.

In order to achieve here a true to scale ratio of lateral width and axial length of the displayed whole-eye scan, real eye parameters are used which are input, measured, calculated or predefined. The eye parameters comprise one or a plurality of the following parameters:

eye section distances between refractive layers,
refractive indices and courses of refractive indices,
axial and lateral resolution of the OCT,
position of the visual axis or fixation axis to the optical axis of the measurement system,
cornea shape and position, lens shape and position such as curvatures, tilting, height and thickness distributions (topography or pachymetry).

Eye part distances to be considered are measured by the data processing unit, are preset, or entered by the user as defined axis lengths or axis length portions.

In a further advantageous configuration of the method according to the invention, the tomographic image of the whole eye is carried out in an anatomically correct manner.

Figure 5:
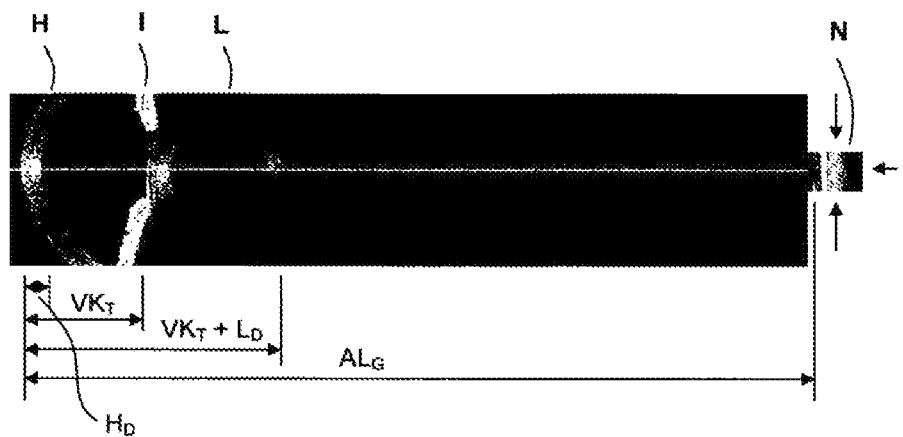
FIG. 5 depicts anatomically correct tomographic images of the whole eye.

In this connection, FIG. 5 shows an anatomically correct image of the whole eye. The structures of the retina N are small compared to the surfaces of the cornea H. The anatomically correct (true to scale) display is based on two or a plurality of correctly dewarped and registered OCT scans. This display is particularly well suited to be used for biometric measurements and for monocular and binocular measurements of eye movements, such as measurements of convergence, fixation movement, nystagmus or the eye position. The overall relation in the whole eye is reproducible for the viewer, in particular if the deviations of the display from the real geometric conditions are less than 10%. For biometric measurement tasks, to some extent, the demands are higher. For example, it should be possible to reproducibly measure axis lengths with an accuracy of at least 50 µm in tissue, and anterior chamber depths with an accuracy of 150 µm in order to achieve acceptable input parameters for matching an IOL with acceptable refraction results.

In a further configuration of the method, tomographically imaging the whole eye is carried out in a diagnostically problem-related manner, wherein axial and/or lateral stretching of eye part portions is carried out while nevertheless maintaining correct eye portion lengths.

The registered and combined display of two or a plurality of OCT scans of the whole eye comprises here an optimized display for a magnified image of one or a plurality of eye portions. In order for the doctor to still be able to quickly and reliably recognize extreme cases such as, for example, excessively long eyes, it should nevertheless be possible to reproduce the eye part portion lengths correctly.

Thus, for example, the doctor is used to a retina display by known OCT devices, which display makes the analysis of layers of the retina easier. It therefore makes sense to display the magnification of the retinal section while maintaining the correct eye portion lengths. The magnification comprises here also an intentional exaggeration of the display of the thickness for a better visibility of pathologies and anatomical conditions. In this connection, the axial magnification can be larger than the lateral magnification. It is absolutely possible here to display other regions such as chamber angle, cornea, lens, vitreous etc. in detail while nevertheless maintaining the adjoining eye portion lengths.

Figure 6:
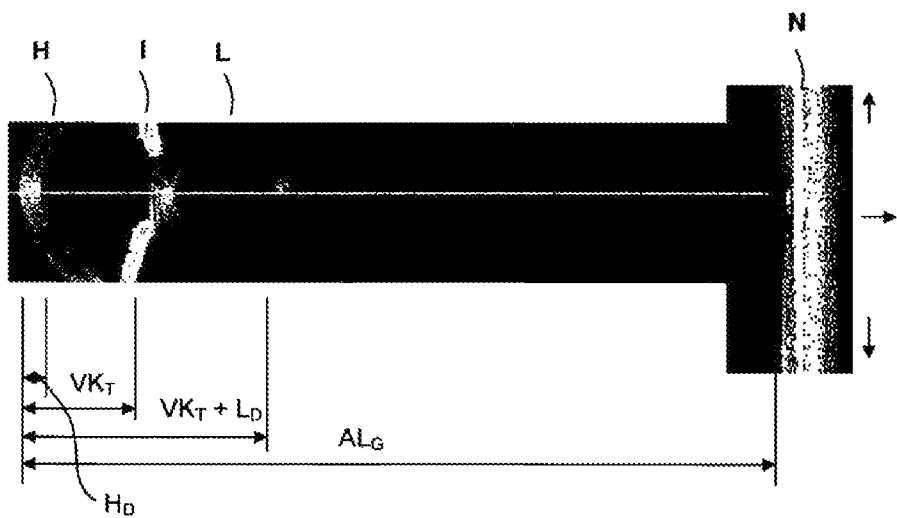
FIG. 6 depicts a diagnostically problem-related tomographic image of the whole eye.

In this connection, FIG. 6 shows a diagnostically problem-related tomographic image of the whole eye. In contrast to the cornea H and the lens L, the structures of the retina N are displayed magnified so that the analysis of the individual layers of the retina N can be made significantly easier. Here too, the diagnostically problem-related display is based on two or a plurality of optically correct dewarped and registered OCT scans.

The combined whole-eye scans are principally also suitable for biometric measurement tasks. The FIGS. 5 and 6 therefore show a selection of relevant measured values such as corneal thickness $H_D$, anterior chamber thickness $VK_T$, lens thickness $L_D$ and total eye length $AL_G$.

While through the magnified display of the retina primarily retinal structures are easier to resolve, a magnified display of the lens makes it easier to examine lens properties such as cataract or lasered micro-incisions etc. In particular, it is also possible to zoom displays of cornea sections so as to enable examinations of granular dystrophy, refractive surgery results, laser incisions, flap cuts or the like.

It is principally also possible here that the tomographic image of the whole eye includes not only a stretching of the retina, or the cornea, or the chamber angle, or the lens, but also a plurality of diagnostic problem areas.

For displaying the tomographic image of the whole eye, according to the invention, a plurality of graphical configuration variants arise.

Thus, the tomographic images of the whole eyes can be displayed as pictures of measured values or as parametric functions of detected boundary surfaces, as grids or line nets or polygons, with or without textures, or in the form of voxel fields.

In particular, it is even possible here to generate the display of the various eye segments in the tomographic image of the whole eye in an identical or different manner, preset, corresponding to an examination mode, or as set by the user.

In the case of the diagnostically problem-related display it can also be of advantage to highlight the display of boundary surfaces/layers with color gradients. This approach is already known and can also be used here.

In a further configuration of the method according to the invention, in addition to two-dimensional whole-eye displays, three-dimensional whole-eye displays are also displayed and can also be combined with each other.

Preferably, a three-dimensional display of the anterior surfaces is carried out by means of a grid structure, and the three-dimensional display of the retina is carried out as a three-dimensional picture by zooming in on the macula. Relevant structure distances, for example from the cornea surface to the retinal pigment epithelium (RPE), are displayed in an anatomically correct manner. Other structural distances can also be scaled in a useful manner for an optimal diagnostic conclusion. For example, the distances between the retina layers can be intentionally enlarged in order to support the visibility of anomalies in the retina also in the case of a whole-eye display on a monitor or on a print-out. The display can also be configured such that the user can configure scaling or shaping of individual or even all eye segments. These configurations can be grid structures and also completely rendered or partially transparent voxel volumes as well as textured grid formats. Also, a region-dependent selection of color scales, for example greyscale negatives in the cornea and lens region, is useful for easier detection of weak signals, while a false-color display in the retinal region allows an easier detection of layered structures.

A preferred configuration comprises a three-dimensional display in which data from two or a plurality of OCT scans has been transferred after optical dewarping into the same coordinate system. These OCT scans can be two- or also three-dimensional. In this coordinate system, the OCT scans can then be displayed together in a free or preset manner, or user-specifically in a rotatable or a displaceable or zoomable manner.

According to a particularly advantageous configuration of the method according to the invention, the tomographic display of the whole eye can take place as a temporally periodically animated display if the data acquisition takes place synchronously or asynchronously to a time-dependent stimulation such as variation of illuminance or of fixation position or fixation imaging.

However, it is also possible to superimpose the display of the whole eye with at least one simulated beam path or a simulated test character display. In particular, it is advantageous here to configure the axial position of the test character display freely selectable or to vary it periodically, for example, to visualize expected refraction errors caused by position-dependent unsharpness.

The tomographic image of the whole eye comprises here the true to scale display of two or a plurality of OCT measurements as a function of time. Thereby, it is preferably possible to implement periodically animated displays (videos or films) which are useful for various ophthalmological diagnoses. This relates, for example, to measurements of the accommodation behavior of the lens, of the anterior chamber depth during accommodation, of the pupil function, of the tear film breaking behavior, of eye movements such as nystagmus, and to measurements during fixation or the line reading behavior.

The stimulation preferably takes place here by superimposing the OCT measuring beam path with fixation-stimulating pictures or targets which are time-dependently presented in lateral or axial displacement or through an image change or through an illuminance change.

Furthermore, it is even possible that the tomographic image of the whole eye is superimposed, textured or color-corrected or, respectively, subtractively or additively combined and displayed with markers such as cursors, lines or form elements, or even with further measurements, wherein this data is linked true to scale with the registered scans. In this connection, defined points or intersection lines or surface areas or volume fields can be identified through said markers. The regions defined in this manner can be displayed together with the OCT display or in further windows as a detail, or a cross-sectional display, or a data array or a numeric display. The displays can contain data from the OCT measurement or from further measurements.

Cursor points, for example, can indicate a data value at a certain position and lines can be used for measuring distances or for marking a cross-sectional profile. Form elements can serve for measuring angles, areas, circumferences and further usual form parameters.

In doing so, parameterized areas as well as non-parameterized data of the whole eye are correctly displayed. Parameterized data can be displayed for the respective eye portion, for example, as a grid with superimposed measurement data or can be displayed individually.

In a further advantageous configuration, the displayed OCT data are superimposed with further measurements or textured or color-corrected or displayed subtractively or additively. Such displays can comprise, for example, the following:
- fundus pictures
- fundus angiographies,
- Scheimpflug images
- reconstructed model data,
- slit lamp pictures,
- perimeter measurements
- polarimetric measurements,
- cornea maps,
- simulations of contact lens fittings,
- contrast agent pictures,
- ultrasound pictures,
- photoacoustically determined data,
- measurement data from functional diagnostics,
- data for describing the refraction, and/or
- data for describing a refractive correction.

Preferably, this data is also linked true to scale with the OCT measurement data.

This configuration can even go so far that the displays are combined with true to scale models of intraocular lenses, anterior chamber lenses, contact lenses, intracorneal lenses, intacs or other usual additions that change the refractive power.

Preferably, as described in all previous points, the true to scale, three-dimensional eye model, which is generated through measurements or known model data and consists of functional eye portions and functional measurements, can be used for any planning and display of operations/operation procedures on or in the eye.

The display of tomographic images of the whole eye can be preset or can be configured by the user. Here, the selection includes the possibility to configure individual eye segments or even the whole image, for example, as a parameter function or a three-dimensional (rendered) voxel data set.

The device according to the invention for recording and displaying an OCT scan, based on swept source optical coherence domain reflectometry (SS OCDR), consists of a tunable laser light source with a measurement range corresponding to the eye length, an interferometer with scan unit, an adjustment mechanism for laterally and/or axially displacing or switching the focus in the eye, a data acquisition unit for acquiring the light fractions backscattered from the sample, and a data processing unit. Here, the data processing unit is designed for combining an OCT whole-eye scan with at least one or a plurality of further overlapping tomographic part-eye or whole-eye scans by using reference information for registering the first whole-eye scan with the further part-eye or whole-eye scans, for evaluating it and displaying it via an existing graphic user interface.

The tunable laser light source which is preferably based on SS OCDR technology is suitable for recording A-scans with a sensitivity of over 90 dB during a measuring time of less than 30 ms, preferred less than 10 ms and particularly preferred less than 1 ms. As is well known to the person skilled in the art, sensitivities can be determined, for example, by determining the signal-to-noise ratio of the maximum measurement signal of a reflector in consideration of the attenuation used.

The existing interferometer with scan unit comprises devices for changing the scan patterns and for varying the reference arm or sample arm lengths in order to implement an OCT whole-eye scan in the form of A-, B- or C-scans of the eye and to transmit it together with one or a plurality of part-eye or whole-eye scan to the data processing unit. The data processing unit registers the individual scans transmitted from the data acquisition unit in consideration of reference information and combines two or a plurality of scans so as to form a tomographic image of the whole eye. The scans can be evaluated and/or displayed via a graphic user interface. Here, different scan patterns with different reference arm or sample arm lengths are used for anterior and posterior scans.

In a first configuration, the data acquisition unit is designed such that further part-eye or whole-eye scans can be acquired, for example, from the following measurements of the topography and can be transmitted to the data processing unit:
- high-resolution ultrasound measurements (UBM),
- SS-OCT (swept source optical coherence tomography) at wavelengths of about 1.3 µm for the anterior eye portion or about 1 µm for the whole eye,
- SD-RT-OCT (spectral domain with spectrometer) at wavelengths of 700 nm to 900 nm, or
- the identical or the same SS-OCT as the first whole-eye scan.

With the tunable laser light source used here, which is based on SS-OCDR technology, it is possible in the A-scan to plot the data along the path of the beam in a depth-resolved scatter profile. Here, the anatomically correct position of the intensity values of the A-scan depends on the actual path of the beam in the eye and thus on one or a plurality of the following parameters which, however, represent only an exemplary (but incomplete) list:
- distance from the eye,
- position of the scan rotation point in the eye,
- eye lengths and eye part distances,
- piercing angle to the refractive layers in the eye,
- refractive indices and course of the refractive indices of the tissue in the eye,
- axial and lateral resolution of the OCT scans,
- numeric sampling of the scans in B- and C-scans,
- position of the visual axis of the eye during the scan,
- ametropia of the eye
- pachymetry and thickness of the cornea and its topography.

As has already been found in the prior art, it is advantageous for OCT scans in the entire eye region to position the measuring beam focus in the eye portion that is to be scanned in each case. With the method according to the invention, it is possible to use different scan patterns with different reference arm lengths of the interferometer for anterior and posterior scans.

The position of the reference plane of the OCT system according to the invention preferably remains the same for anterior and posterior OCT scans; however, it can also be configured to be discretely switchable or continuously variable, for example for minimizing signal drops. Preferably, even in the case of variations of the position of the reference plane, the reference arm length of the interferometer is kept constant while the sample arm length is changed, as a result of which the signal stability is increased.

In contrast to this, the polarization settings of the two or more scans can differ from each other in order to optimize the signal conditions in the individual scan.

The fixation of the eye is preferably centered and the B-scans preferably intersect the visual axis of the eye in the region of the cornea apex. Refixings for increasing the likelihood of generating specular boundary surface reflexes with high signal strength are possible but are not absolutely necessary.

For measuring the whole eye, apart from A-scans, it is also possible to use B- or C-scans with different scan patterns in the lateral direction such as, for example, line and curvature scans, meridian or star scans, circle scans, spiral scans, block scans etc. As mentioned, apart from the lateral scan configuration, focusing-dependent beam divergences and depth-dependent location and angle variations are also essential characteristics of a scan process.

To this, FIG. 1 and FIG. 2 show two exemplary line scan processes in the anterior and posterior eye region with the associated B-scans which range from whole scans to high-resolution scans layered along the optical axis. These two scan patterns already show a greatly differing beam path during scanning and also in terms of the beam shape.

FIG. 1 shows a possible scan process for an anterior scan, the focusing of which lies in the anterior eye portion so as to be able to generate there a good spatial resolution. The scanning beam runs through the cornea H and the lens L up and onto the retina N, wherein S characterizes the visual axis, and I characterizes the iris. While in the upper part a possible beam path in dependence of the distances of the eye layers is schematically illustrated, the lower part shows the associated B-scan. In the B-scan, the good spatial resolution of the anterior eye portions is shown while the retina is visible as a line, but actually is primarily an angularly resolved and not a spatially resolved image of the fovea. For the anterior scan, usually, a parallel or preferably a telecentric scan pattern is used.

In contrast to this, FIG. 2 shows a possible scan process of a posterior scan. Here too, the upper part illustrates the possible beam path of a posterior scan which, as it is known from the prior art, has a scan rotation point in the pupil plane. The lower picture shows again the associated B-scan. The scanning beam runs through the cornea H and the lens L up to and onto the cornea N, wherein S characterizes the visual axis, and I characterizes the iris. Since due to the widened beam and the scan pattern primarily no spatial resolution but primarily an angular resolution can be achieved in the anterior eye portions, the cornea and lens reflexes are only visible as line-like boundary surface reflexes. However, the retina located in the focus of the scanning beam can be displayed in a spatially resolved manner.

Thus, the focus of the scan preferably lies axially in the region that is in each case better suited for lateral resolution, i.e., in the case of the anterior scan in the vicinity of the anterior lens surface and in the case of the posterior scan in the vicinity of the retina.

The lateral width of the boundary surface structures in the scans depends in this arrangement on the entered or measured or predefined eye parameters. According to the invention, the eye parameters comprise one or a plurality of the following parameters:
- eye lengths or eye part distances,
- refractive indices and course of the refractive indices,
- axial and lateral resolution of the OCT scans,
- position of the visual axis to the optical axis of the measurement system,
- topography or
- pachymetry of the eye.

In this context it is known to the person skilled in the art that refractive indices are to be understood as group velocity indices which are suitable for determining geometrical lengths from optical delays in consideration of dispersion.

The axial and lateral resolutions of the OCT system are considered here as eye parameters because the effective resolution in different regions of the eye depends on the geometric and optical conditions in the eye. For example, the lateral optical resolution in the region of the retina in a myopic eye is lower than in an emmetropic eye because here, defocusing takes place in the myopic eye. This can be taken into account when combining scans in order to implement the best possible displays of the eye with regard to resolution and signal strength.

In a second advantageous configuration, the data processing unit is suitable for registering the first whole-eye scan and the further part-eye or whole-eye scans with each other, for which corresponding reference information is required.

Furthermore, for this purpose, the data processing unit is capable of obtaining the reference information from the position detection of corresponding structures in the scan and/or from the relation of the optical axis of the measurement system to the eye, and comprises for this purpose a storage unit and/or a calculating unit and/or an input unit.

Examples for important reference information are information about the position and curvature of the anterior cornea surface and the distance thereof from the RPE layer in the fovea centralis, which information is needed for optical dewarping and an anatomically correct display. In this context, the specular boundary surface reflexes, in particular of front and back surfaces of cornea and eye lens or of the retina, which are easily detectable in the first and further OCT scans, are suitable as reference information. However, said reference information about the optical axis of the measurement system can also comprise offsets from calibration data, alignment data of measurement devices or user input data.

The eye part distances which are used here for the entire or partial correction of the overall displays can comprise, for example:
- the total length of the eye (distance from cornea to retina),
- the depth of the anterior chamber (distance from cornea to the front side of the lens),
- the cornea thickness or pachymetry,
- the lens thickness, or
- the distance from the lens to the retina.

In a particular configuration, the eye section distances can also be originated from the detection of the boundary surfaces of the OCT scan itself.

In the preferred case, registering is carried out over at least one SS OCT whole-eye scan with one or a plurality of further part-eye or whole-eye scans by means of registering via reference information. Registering the individual scans is carried out in axial and/or lateral and/or rotatory manner and in consideration of information.

The visual axis, which is determined in the measurement device through the position of the fixation target, is indicative for the position of the optical axis of the measurement device in relation to the eye. If the positional relation between optical axis of the measurement device and the fixation axis of the eye is known, one or a plurality of OCT scans can be registered. At least 2 reference points and the optical axis of the two OCT scans must be known.

In the preferred case, the 2 points include specular boundary surface reflexes which can be detected in the scans to be registered. The specular reflexes can be detected in a whole-eye scan with anterior and also posterior modalities. They can be registered with known reference points of cornea vertex, fovea and further reference points.

Furthermore, it is also preferred that in addition an offset can be used for registering. This lateral or axial offset can consist of calibration, switching the scan modality, and entered x-, y- and z-coordinates. Data input, for example of stored calibration data or measured alignment data of measurement devices, can take place via user input or through a hardware or software data interface.

In this connection, FIG. 3 shows two possibilities for registering 2 OCT scans. Here, the registration is dependent on the position of the fixation axis (visual axis) in relation to the eye. Based on the fixation target F and the fixation axis, a conclusion is drawn on the position of the optical axis of the measurement device in relation to the cornea vertex V of the eye.

In the upper variant illustrated in FIG. 3, the fixation axis of the eye coincides with the optical axis of the measurement device so that the fixation target F likewise lies on the optical axis of the measurement device.

In contrast to this, in the lower variant shown in FIG. 4, the optical axis does not lie on the fixation axis. For registering the individual scans (A–A2 and B1–B2=), the distance b of the fixation target F from the optical axis and also the distance a of the eye from the measurement device or from the fixation target F have to be determined.

With the knowledge about the position of the fixation axis in relation to the eye, all scans can be registered to each other:
A1 and A2,
A1 and B2,
B1 and A2 or
B1 and B2.

Registration of the individual scans is carried out, for example, axially, i.e., along the optical axis or fixation axis, wherein anterior and posterior reflexes are used for this purpose. While the anterior reflex comprises the corneal vertex reflex, the posterior reflex comprises the fovea reflex of the retina.

It is particularly advantageous if most of the B-scans, ideally each of the B-scans (the A-scans of which each run through the entire depth of the eye) runs through the vertex of the cornea or through the piercing point of the visual axis through the cornea. In this case it is ensured that each B-scan includes anterior and posterior reflexes of defined eye part length portions which are used for axial registration.

It can be useful to select those B-scans from the measured B-scan which comply with the above advantageous condition. This can be controlled by monitoring the fixation state or the topography/keratometry as part of the lateral and rotatory registration during the recording of the B-scan.

Also, for the lateral registration with central patient fixation, the evaluation of simple reflexes such as fovea reflex and cornea vertex reflex is sufficient. Advantageously, the reflexes are detected from the OCT scans themselves, e.g., through threshold observation of scattering intensities and/or edge recognition and/or layer segmentations.

In contrast to lateral registration, rotatory registration of scan requires extraction of features from lateral structures or surfaces. For this, primarily iris structures, scleral blood vessel structures, boundary surface shapes or also topographies are evaluated.

While the iris or blood vessel structures are obtained from images recorded parallel or intermittent to the OCT scans, the boundary surface shapes can be obtained from the OCT scans themselves.

If topographies of the eye are to be evaluated for the rotatory registration, they can be recorded by means of Placido disk systems or can be retrieved for the respective eye.

In particular for possible medical applications it is important that displays of body parts, in particular of parts of the eye, are represented in an anatomically correct manner so as to be comparable, for example, with histological sections. Of course, this applies also to tomographic images in the form of OCT scans.

As has already been found in the prior art, the comparison of data of different eyes or of a plurality of measurements of the same eye is often only useful in the case of dewarped displays. Since this applies in particular also to OCT scans and due to the inevitably incorrect results, combining two of the described OCT scans makes little sense without a prior correct optical dewarping, or could even result in misinterpretation of diagnoses because structures located posterior to refractive surfaces can appear as being unusually deformed. The line display of the angularly resolved fovea in FIG. 1, which can easily be misinterpreted, has already been mentioned as an example.

For displaying the whole eye, an OCDR or OCT whole-eye scan, consisting of one or a plurality of A-scans which have to comprise the whole eye, is combined with one or a plurality of anterior and posterior B- or C-scans which consist of a plurality of laterally displaced A-scans, wherein each A-scan can comprise a part of the eye or also the entire eye length.

In a further advantageous configuration, the data processing unit is capable of initiating further tomographic part-eye or whole-eye scans which exhibit an overlap with the first whole-eye scan in the axial direction of at least 25 mm, but preferred of more than 32 mm, particularly preferred of more than 40 mm (geometrical lengths).

Such an overlap means that in all scans to be registered anterior structures (e.g. of the cornea or lens) as well as posterior structures (e.g. of the retina) are detectable, even if these structures possibly do not exhibit in all scans a quality suitable for the display. However, if in all scans to be combined the reference structures are contained, for example, in the form of boundary surface signals from the anterior and posterior eye regions, a particularly secure and highly accurate registration between the scans themselves can take place. Due to the redundancy and averaging effect, the simultaneous availability of anterior and posterior reference structures enables increased accuracy and increased reliability, for example, also through consistency considerations with a limited acceptable range.

The required minimal overlap length of 25 mm allows such a registration of a majority of the patients, in particular such patients with emmetropic and hyperopic eyes, since the average eye length is approx. 24 mm. With an overlap of at least 32 mm, nearly all patients can be considered, thus also those with pronounced axial myopia. Furthermore, with overlap lengths of over 40 mm it is also possible to cover extreme cases which, however, are rather rare (for example, buphthalmos).

Another advantage of the combination of OCT scans with overlaps>25 mm is that in the case of a common display, a delimitation of anterior and posterior scans arranged in a row in both scans can be defined in a common space in which there are no relevant structures so that with regard to matching an IOL, no loss of information occurs. Such losses of information can occur if there would be signals of the cornea, retina or of natural or artificial eye lenses at the delimitation line of the scans to be combined.

The region for an advantageous delimitation can be defined, among other things, through the detection of the noise level. Suitable regions are regions between the boundary surfaces in which little/no volume scattering is detected, as, for example, in the vitreous. The delimitation between the scans does not have to correspond to a straight line but can be free in terms of the shape. If signals in the vitreous hinder such a definition of the delimitation between the scans, for example, as a result of hemorrhaging, the delimitation can also be carried out with regard to the cornea and the known or expected eye length in the vitreous region.

As a requirement for correct dewarping it is assumed for all OCT scans that the beam path of the measurement system in front of the cornea is known through calibration of the OCT scanner or through measurements on a reference object. Subsequently, optical dewarping as a requirement for correct registration of the individual scans can be carried out in the axial and lateral directions so that the beam paths of the scans are known with regard to a common coordinate system.

For this, the data processing unit in a next advantageous configuration is capable of carrying out the registration of the individual scans, which are transmitted from the data acquisition unit, in an axial and/or lateral and/or rotatory manner and in consideration of eye part distances, wherein the individual scans were correctly spatially dewarped by means of optical ray tracing during the refraction on detected boundary surfaces. Here, the known paths of the measuring beams are viewed during the scan up to the first refractive surface (cornea). Taking into account the known, measured or estimated shape of the refractive surface (at least 2-dimensional, preferably 3-dimensional) and the assumed or measured refraction index transition, now, the angle and divergence changes in the individual measuring beam paths are calculated by using, for example, the Snell's law of refraction or the Fermat's principle, so that depending on the depth, the signals of the A-scan can be allocated correct lateral spatial information. These considerations can now be continued on further refractive structures up to the retina (natural crystal lens, IOL). By considering measured or estimated refractive indices between the boundary surfaces, it is possible, in turn, to correct the eye part distances between the boundary surfaces in such a manner that they are geometrically correct. If, in some cases, the boundary surfaces cannot be detected, for example, because only parts are scanned or because highly absorbent tissue parts or scattering tissue parts cause shading, then, detected boundary surface parts are preferably interpolated and are extrapolated at least up to the A-scan which runs through the pupil margin. Otherwise, no correct dewarping of the scanned parts of the posterior eye portion is possible and there is the risk of generating artifacts. Suited for this are mathematical functions such as, for example, polynomials, splines or Fourier series.

With the lateral information allocated in this manner to the A-scan and with axial corrections, it is now possible by entering intensity signals into a common coordinate system to register correctly dewarped part-eye or whole eye B-scans to each other. It is possible here to average the intensity values of the individual scans in a weighted manner or to select them according to criteria such as the local signal-to-noise ratio.

It is also to be considered that in the case of the consideration of directional changes due to refraction and also in the case of axial corrections of distances, the dispersion of the refractive index of the tissue in dependence on the wavelength of the measuring beam should be taken into account. This wavelength of the measuring beam can also vary between the individual part-eye or whole-eye scans. For example, a whole-eye scan is preferably implemented with measurement radiation in the range between 1030 and 1090 nm, whereas the anterior eye portion is preferably measured in the range of from 1250 . . . 1400 nm or 750 . . . 900 nm, and the posterior eye portion is preferably measured in the range of from 750 . . . 900 nm.

For the case that the keratometry or topography of the cornea is known, it is possible through ray tracing to precisely determine the corrected ray path. In the best case, the accommodation state of the lens is also determined in the one or a plurality of scans, or is determined through simulation. Here, ray tracing is used for all A-scans. By considering the optical properties of boundary surfaces in the eye, the ray tracing along the ray propagation direction performed for each A-scan is utilized for spatial dewarping the B- or C-scan.

For dewarping, one or a plurality of the above-mentioned parameters can be used. These parameters can be determined from the OCT scan or can be originated from other measurements, or can be defined and set by the user.

In this connection, FIG. 4 shows two registered OCT scans to be combined. While the upper image shows the anterior whole-eye scan in the form of a B-scan, the lower image illustrates a posterior whole-eye scan, likewise as a B-scan. Here, H designates the cornea, L the lens, N the retina, S the visual axis and I designates the iris of the eye.

As is already shown in the FIGS. 1 and 2, the focusing lies always in the eye portion of which a good resolution is to be generated. The B-scan displayed in the upper image shows the anterior whole-eye scan in which the anterior eye portions exhibit a good spatial resolution. In contrast, the lower image shows the B-scan of the posterior whole-eye scan in which the retina is displayed in a good spatial resolution.

After the individual scans transmitted by the data processing unit have been registered in consideration of eye section distances, two or a plurality of scans can be combined to form a tomographic image of the whole eye. According to FIG. 4, this can be carried out in that the partial images with good spatial resolution are combined to form a tomographic image of the whole eye, wherein a plurality of different display possibilities arise.

Thus, the beam path of both scans is known in a common coordinate system from which a dewarped whole-eye scan can be calculated, for example, by replacing the region of the retina in the dewarped anterior scan by the corresponding region in the dewarped posterior scan.

In order to achieve here a true to scale ratio of lateral width and axial length of the displayed whole-eye scan, real eye parameters are used which are input, measured, calculated or predefined. The eye parameters comprise one or a plurality of the following parameters:

eye section distances between refractive layers,
refractive indices and courses of refractive indices,
axial and lateral resolution of the OCT,
position of the visual axis or fixation axis to the optical axis of the measurement system, cornea shape and position, lens shape and position such as curvatures, tilting, height and thickness distributions (topography or pachymetry).

Eye part distances to be considered are measured by the data processing unit, are preset, or entered by the user as defined axis lengths or axis length portions.

In a further advantageous configuration of the device according to the invention, the data processing unit is capable of generating anatomically correct or diagnostically problem-related, tomographic whole-eye scans and of displaying them via the graphical user interface.

In this connection, FIG. 5 shows an anatomically correct image of the whole eye. The structures of the retina N are small compared to the surfaces of the cornea H. The anatomically correct (true to scale) display is based on two or a plurality of correctly dewarped and registered OCT scans. This display is particularly well suited to be used for biometric measurements and for monocular and binocular measurements of eye movements, such as measurements of convergence, fixation movement, nystagmus or the eye position. The overall relation in the whole eye is reproducible for the viewer, in particular if the deviations of the display from the real geometric conditions are less than 10%. For biometric measurement tasks, to some extent, the demands are higher. For example, it should be possible to reproducibly measure axis lengths with an accuracy of at least 50 µm in tissue and anterior chamber depths with an accuracy of 150 µm in order to achieve acceptable input parameters for matching an IOL with acceptable refraction results.

In the case of the problem-related generation and display of a tomographic whole-eye scan, axial and/or lateral stretching of eye part portions is carried out while nevertheless maintaining correct eye portion lengths.

The registered and combined display of two or a plurality of OCT scans of the whole eye comprises here an optimized display for a magnified image of one or a plurality of eye portions. In order for the doctor to still be able to quickly and reliably recognize extreme cases such as, for example, excessively long eyes, it should nevertheless be possible to reproduce the eye part portion lengths correctly.

Thus, for example, the doctor is used to a retina display by known OCT devices, which display makes the analysis of layers of the retina easier. It therefore makes sense to display the magnification of the retinal section while maintaining the correct eye portion lengths with regard to the RPE. The magnification comprises here also an intentional exaggeration of the display of the thickness for a better visibility of pathologies and anatomical conditions. In this connection, the axial magnification can be larger than the lateral magnification. It is absolutely possible here to display also other regions such as chamber angle, cornea, lens, vitreous etc. in detail while nevertheless correctly displaying relevant distances from other eye parts (for example the distance from chamber angle to chamber angle).

In this connection, FIG. 6 shows a diagnostically problem-related tomographic image of the whole eye. In contrast to the cornea H and the lens L, the structures of the retina N are displayed magnified so that the analysis of the individual layers of the retina N can be made significantly easier. Here too, the diagnostically problem-related display is based on two or a plurality of optically correct dewarped and registered OCT scans.

The combined whole-eye scans are principally also suitable for biometric measurement tasks. The FIGS. 5 and 6 therefore show a selection of relevant measured values such as corneal thickness $H_D$, anterior chamber thickness $VK_T$, lens thickness $L_D$ and total eye length $AL_G$.

If in problem-related displays of the whole eye with locally adapted scaling of scan parts, manually displaceable measurement marks are also used for determining the length, then, preferably, the relative position of the registered scans and the possibly different magnification scales in the scan parts are considered in such a manner that nevertheless correct length measurements between the measurement marks are achieved.

While through the magnified display of the retina primarily retinal structures are easier to resolve, a magnified display of the lens makes it easier to examine lens properties such as cataract or lasered micro-incisions etc. In particular, it is also possible to zoom displays of cornea sections so as to enable examinations of granular dystrophy, refractive surgery results, laser incisions, flap cuts or the like.

It is principally also possible here that the tomographic image of the whole eye includes not only a stretching of the retina, or the cornea, or the chamber angle, or the lens, but also a plurality of diagnostic problem areas.

For displaying the tomographic image of the whole eye, according to the invention, a plurality of graphical configuration variants arise.

In a further advantageous configuration of the device, the data processing unit is capable of superimposing grid or polygon displays of boundary surfaces with further measurements, of combining them textured or color-corrected or, respectively, subtractively or additively, and of displaying them true to scale via the graphic user interface. Moreover, the tomographic whole-eye scans can be generated by the data processing unit as measurement data pictures or as parametric functions of detected boundary surfaces, as grids or line nets or polygons, with or without textures, or in the form of voxel fields, and can be displayed via the graphic user interface.

In particular, it is even possible here to generate the display of the various eye segments in the tomographic image of the whole eye in an identical or different manner, preset, corresponding to an examination mode, or as set by the user.

In the case of the diagnostically problem-related display it can also be of advantage to highlight the display of boundary surfaces/layers with color gradients. This approach is already known and can also be used here.

In a further configuration variant of the device, in addition to two-dimensional whole-eye displays, three-dimensional whole-eye displays can also be displayed by the data processing unit and can also be combined with each other.

Preferably, a three-dimensional display of the anterior surfaces is carried out by means of a grid structure, and the three-dimensional display of the retina is carried out as a three-dimensional picture by zooming in on the macula. Relevant structure distances, for example from the cornea surface to the retinal pigment epithelium (RPE), are displayed in an anatomically correct manner. Other structural distances can also be scaled in a useful manner for an optimal diagnostic conclusion. For example, the distances between the retina layers can be intentionally enlarged in order to support the visibility of anomalies in the retina also in the case of a whole-eye display on a monitor or on a print-out. The display can also be configured such that the user can configure scaling or shaping of individual or even all eye segments. These configurations can be grid structures and also completely rendered or partially transparent voxel volumes as well as textured grid formats. Also, a region-dependent selection of color scales, for example greyscale negatives in the cornea and lens region, is useful for easier detection of weak signals, while a false-color display in the retinal region allows an easier detection of layered structures.

A preferred configuration comprises a three-dimensional display in which data from two or a plurality of OCT scans has been transferred after optical dewarping into the same coordinate system. These OCT scans can be two- or also three-dimensional. In this coordinate system, the OCT scans can then be displayed together in a free or preset manner, or user-specifically in a rotatable or a displaceable or zoomable manner.

According to a particularly advantageous configuration of the device, the tomographic display of the whole eye can take place as a temporally periodically animated display if the data acquisition takes place synchronously or asynchronously to a time-dependent stimulation such as the variation of illuminance or of fixation position or fixation imaging.

However, it is also possible to superimpose the display of the whole eye with at least one simulated beam path or a simulated test character display. In particular, it is advantageous here to configure the axial position of the test character display freely selectable or to vary it periodically, for example, to visualize expected refraction errors caused by position-dependent unsharpness.

The tomographic image of the whole eye comprises here the true to scale display of two or a plurality of OCT measurements as a function of time. Thereby, it is preferably possible to implement periodically animated displays (videos or films) which are useful for various ophthalmological diagnoses. This relates, for example, to measurements of the accommodation behavior of the lens, of the anterior chamber depth during accommodation, of the pupil function, of the tear film breaking behavior, of eye movements such as nystagmus, and to measurements during fixation or the line reading behavior.

The stimulation preferably takes place here by superimposing the OCT measuring beam path with fixation-stimulating pictures or targets which are time-dependently presented in lateral or axial displacement or through an image change or through an illuminance change.

Furthermore, it is even possible that the tomographic image of the whole eye is superimposed, textured or color-corrected or, respectively, subtractively or additively combined and displayed with markers such as cursors, lines or form elements, or even with further measurements, wherein this data is linked true to scale with the registered scans. In this connection, defined points or intersection lines or surface areas or volume fields can be identified through said markers. The regions defined in this manner can be displayed together with the OCT display or in further windows as a detail, or a cross-sectional display, or a data array or a numeric display. The displays can contain data from the OCT measurement or from further measurements.

Cursor points, for example, can indicate a data value at a certain position and lines can be used for measuring distances or for marking a cross-sectional profile. Form elements can serve for measuring angles, areas, circumferences and further usual form parameters.

In doing so, parameterized areas as well as non-parameterized data of the whole eye are correctly displayed. Parameterized data can be displayed for the respective eye portion, for example, as a grid with superimposed measurement data or can be displayed individually.

In a further advantageous configuration, the displayed OCT data are superimposed with further measurements or are textured or color-corrected or displayed subtractively or additively. Such displays can comprise, for example, the following:
fundus pictures
fundus angiographies,
Scheimpflug images
reconstructed model data,
slit lamp pictures,
perimeter measurements
polarimetric measurements,
cornea maps,
simulations of contact lens fittings,
contrast agent pictures,
ultrasound pictures,
photoacoustically determined data,
measurement data from functional diagnostics,
data for describing the refraction, and/or
data for describing a refractive correction.

Preferably, this data is also linked true to scale with the OCT measurement data.

This configuration can even go so far that the displays are combined with true to scale models of intraocular lenses, anterior chamber lenses, contact lenses, intracorneal lenses, intacs or other usual additions that change the refractive power.

Preferably, as described in all previous points, the true to scale, three-dimensional eye model, which is generated through measurements or known model data and consists of functional eye portions and functional measurements, can be used for any planning and display of operations/operation procedures on or in the eye.

The display of tomographic images of the whole eye can be preset or can be configured by the user. Here, the selection includes the possibility to configure individual eye segments or even the whole image, for example, as a parameter function or a three-dimensional (rendered) voxel data set.

With the invention, a solution for displaying tomographic images of the whole eye is made available which eliminates the disadvantages of the solutions of the known prior art. The display of all regions of the whole eye contains depth-resolved high-precision measurement data based on interferometric measurement methods. Displaying the tomographic images of the whole eye can be carried out in an anatomically correct manner, i.e., with correct dimensions and distances of the individual eye segments, or diagnostically problem-related, i.e., with axial and/or lateral stretching of eye part portions while nevertheless maintaining correct eye portion lengths.

In addition, the invention offers the possibility to reconstruct the whole eye as a three-dimensional optical model based on "in vivo" measurement data and, at the same time, to ensure also image-supported examinations of part sections.

It is possible by suitably marking points of the three-dimensional tomographic images of the whole eye that the user is readily able to measure intensity values, length dimensions and other properties in an optically correct and dewarped manner.

With the invention, parameterized surfaces as well as non-parameterized data of the whole eye can be displayed correctly. Parameterized data can be displayed for the respective eye portion, e.g., as a grid and can be superimposed to the measurement data, or can be displayed individually.

With the proposed solution it is also possible, prior to a surgery, to design a three-dimensional eye model for performing and/or monitoring surgery. Through appropriate online measurements it could even be possible to monitor the eye surgery online, for example, via a display, in particular a head-up display. This can significantly simplify the planning as well as the execution of a surgery.

Furthermore, it is possible with the proposed solution to plot, in particular in a semi-transparent manner, a path of at least one beam bundle, which is simulated, for example, by means of ray tracing, into an anatomically correct eye display according to the invention so as to visualize existing or expected image proportions. In this connection, the calculated display of a simulated test character on the retina is preferably superimposed with the display of the retina so as to visualize the quality of the calculated image proportions. Also, the axial position of the test character display ("E") in the three-dimensional display can preferably be varied by the user or is automatically animated so as to visualize the tendency of the optimal image to deviate from the plane of the retinal pigment epithelium.

The invention claimed is:

1. A method for recording and displaying an OCT whole-eye scan based on swept source optical coherence reflectometry (SS OCDR), comprising:
   illuminating the eye with a laser beam of a tunable laser light source having a measurement range corresponding to an eye length of an eye;
   displacing a focus of the laser beam in the eye laterally and/or axially by an adjustment mechanism;
   capturing the light fractions backscattered from the eye via an interferometer with a scan unit;
   converting the light fractions to data by a data acquisition unit;
   transferring the data to a data processing unit;
   wherein the data processing unit combines an OCT whole-eye scan with at least one overlapping tomographic part-eye or whole-eye scan using reference information to register the first whole-eye scan with further part-eye or whole-eye scans, and evaluates and/or displays the combined whole-eye scan on a user interface.

2. The method according to claim 1, further comprising obtaining the further part-eye or whole-eye scans based on identical or the same SS OCDR, an ultrasound measurement, a confocal scan or other OCT systems.

3. The method according to claim 1, further comprising using different scan patterns with different reference arm or sample arm lengths of the interferometer for anterior and posterior scans.

4. The method according to claim 1, wherein overlap between the first whole-eye scan and the further part-eye or whole-eye scans is at least 25 mm in an axial direction.

5. The method according to claim 1, wherein overlap between the first whole-eye scan and the further part-eye or whole-eye scans is more than 32 mm in an axial direction.

6. The method according to claim 1, wherein overlap between the first whole-eye scan and the further part-eye or whole-eye scans is more than 40 mm in an axial direction.

7. The method according to claim 1, further comprising obtaining the reference information from one or a plurality of the following sources:
   from the position detection of corresponding structures in the scans, and
   the relation of the optical axis of the measurement system to the eye obtained from the data of a storage unit, a calculating unit or an input unit.

8. The method according to claim 7, wherein the reference information contains specular boundary surface reflections detected in the first and the further OCT scans.

9. The method according to claim 7, wherein the reference information on the optical axis of the measurement system comprises offsets from calibration data, alignment data of measurement devices or user input data.

10. The method according to claim 1, further comprising registering the individual scans transmitted from the data acquisition unit axially, laterally, rotatory or a combination of the foregoing and in consideration of eye part distances.

11. The method according to claim 10, further comprising, for registering, correctly spatially dewarping the individual scans by optical ray tracing at boundary surfaces that are detected and laterally extrapolated at least up to the pupil margin.

12. The method according to claim 1, further comprising basing a ratio of lateral width and axial length of the displayed whole-eye scan on entered or measured or calculated or predefined eye parameters to achieve true scale.

13. The method according to claim 12, wherein the eye parameters comprise one or a plurality of the following parameters: eye part distances between refractive layers, refractive indices and courses of refractive indices, axial and lateral resolution of the OCT, position of the visual axis/fixation axis relative to the optical axis of the measurement system, cornea shape and position, lens shape and position such as curvatures, tilting, height and thickness distributions.

14. The method according to claim 13, wherein the eye part distances to be considered by the data processing unit are measured, preset, or are entered by the user as defined axis lengths or axis length portions.

15. The method according to claim 12, wherein tomographically imaging the whole eye is carried out in an anatomically correct manner.

16. The method according to claim 12, wherein tomographically imaging the whole eye is carried out in a diagnostically problem-related manner.

17. The method according to claim 12, further comprising displaying a tomographic image of the whole eye as measurement data pictures or as parametric functions of detected boundary surfaces, as grids or line nets or polygons, with or without textures, or in the form of voxel fields.

18. The method according to claim 12, further comprising overlapping the anatomically correct display of the whole eye with at least one simulated beam path or a simulated test character display.

19. The method according to claim 12, wherein the grid or polygon displays of boundary surfaces are superimposed with further measurements, are textured or color-corrected or, respectively, are subtractively or additively combined and displayed, wherein the data are linked true to scale with the registered scans.

20. A device for recording and displaying an OCT whole-eye scan based on swept source optical coherence reflectometry (SS OCDR), said device comprising:
   a tunable laser light source having a measurement range corresponding to a length of the eye;
   an interferometer with scan unit;
   an adjustment mechanism that laterally and/or axially displaces or switches the focus in the eye;
   a data acquisition unit that acquires the light fractions backscattered from the sample; and
   a data processing unit, wherein the data processing unit combines an OCT whole-eye scan with at least one further overlapping tomographic part-eye or whole-eye scan by using reference information for registering the first whole-eye scan with the further part-eye or whole-eye scans, and the data processing unit comprises a graphical user interface for evaluating and/or displaying the combined whole-eye scan.

21. The device according to claim 20, wherein the tunable laser light source records A-scans with a sensitivity above 90 dB during a measurement time of less than 30 ms.

22. The device according to claim 21, wherein the tunable laser light source records A-scans with a sensitivity above 90 dB during a measurement time of less than 10 ms.

23. The device according to claim 21, wherein the tunable laser light source records A-scans with a sensitivity above 90 dB during a measurement time of less than 1 ms.

24. The device according to claim 20, wherein the interferometer further comprises devices that change the scan patterns and that vary the reference arm or sample arm length.

25. The device according to claim 20, wherein the data acquisition unit is designed such that further part-eye or whole-eye scans can be acquired from the identical or same SS OCDR, from an ultrasound measurement, a confocal scan or from other OCT systems and can be transferred to the data processing unit.

26. The device according to claim 20, wherein the data processing unit is designed for initiating further tomographic part-eye or whole-eye scans which exhibit an overlap with the first whole-eye scan in the axial direction of at least 25 mm.

27. The device according to claim 26, wherein the data processing unit is designed for initiating further tomographic part-eye or whole-eye scans which exhibit an overlap with the first whole-eye scan in the axial direction of more than 32 mm.

28. The device according to claim 26, wherein the data processing unit is designed for initiating further tomographic part-eye or whole-eye scans which exhibit an overlap with the first whole-eye scan in the axial direction of more than 40 mm.

29. The device according to claim 26, wherein the data processing unit is designed for obtaining the reference information from position detection of corresponding structures in the scans and/or from the relation of the optical axis of the measurement system to the eye, and comprises for this purpose a storage unit and/or a calculating unit and/or an input unit.

30. The device according to claim 26, wherein the reference information transferred to the data processing unit contains specular boundary surface reflections detected in a first and further scans.

31. The device according to claim 26, wherein the reference information on the optical axis of the measurement system transmitted to the data processing unit comprises offsets from calibration data, alignment data of measurement devices or user input data.

32. The device according to claim 26, wherein the data processing unit carries out the registration of individual scans transmitted from the data acquisition unit in an axial and/or lateral and/or rotatory manner and in consideration of eye part distances, wherein the individual scans have been correctly spatially dewarped by optical ray tracing at boundary surfaces that are detected and laterally extrapolated at least up to the pupil margin.

33. The device according to claim 26, wherein the data processing unit generates anatomically correct or diagnostically problem-related, tomographic whole-eye scans and displays the whole eye scans on the graphical user interface.

34. The device according to claim 26, wherein the data processing unit superimposes grid or polygon displays of boundary surfaces with further measurements, combines the displays of boundary surfaces textured or color-corrected, or, respectively, subtractively or additively, and displays them true to scale via the graphical user interface.

35. The device according to claim 26, wherein the data processing unit generates the tomographic whole-eye scans as measurement data pictures or as parametric functions of detected boundary surfaces, as grids or line nets or polygons, with or without textures, or in the form of voxel fields, and displays them via the graphical user interface.

36. The device according to claim 26, wherein the data processing unit superimposes the tomographic whole-eye scans with at least one simulated beam path or a simulated test character display and displays them via the graphical user interface.

37. The device according to claim 34, wherein the graphical user interface, with the aid of entered or measured or calculated or predefined eye parameters, displays whole-eye scans with a true to scale ratio of lateral width and axial length.

* * * * *